United States Patent
Auth

(10) Patent No.: US 7,637,929 B2
(45) Date of Patent: Dec. 29, 2009

(54) SELF-DRILLING BONE SCREW

(75) Inventor: Stefan Auth, Merdingen (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 963 days.

(21) Appl. No.: 11/008,343

(22) Filed: Dec. 9, 2004

(65) Prior Publication Data
US 2005/0137598 A1 Jun. 23, 2005

(30) Foreign Application Priority Data
Dec. 23, 2003 (DE) ................. 103 61 044

(51) Int. Cl.
A61B 17/84 (2006.01)
(52) U.S. Cl. .................................. 606/311
(58) Field of Classification Search ............... 606/72, 606/73; 411/411, 426, 386
See application file for complete search history.

(56) References Cited

U.S. PATENT DOCUMENTS

| | | | |
|---|---|---|---|
| 4,903,691 A | | 2/1990 | Heinl |
| 5,300,076 A | * | 4/1994 | Leriche .................. 606/73 |
| 5,882,161 A | * | 3/1999 | Birkelbach ............ 411/387.7 |
| 5,925,048 A | | 7/1999 | Ahmad et al. |
| 6,221,075 B1 | | 4/2001 | Tormala et al. |
| 6,565,573 B1 | * | 5/2003 | Ferrante et al. ............. 606/73 |
| 6,692,498 B1 | * | 2/2004 | Niiranen et al. ............. 606/69 |
| 2001/0004694 A1 | * | 6/2001 | Carchidi et al. ............. 606/73 |
| 2003/0210970 A1 | * | 11/2003 | Bechtel et al. ............ 411/411 |
| 2004/0044345 A1 | * | 3/2004 | DeMoss et al. ............. 606/73 |
| 2004/0122426 A1 | * | 6/2004 | Michelson .................. 606/61 |
| 2005/0021036 A1 | * | 1/2005 | Whitmore et al. ........... 606/73 |

FOREIGN PATENT DOCUMENTS

| | | |
|---|---|---|
| DE | 29520312 | 3/1996 |
| DE | 19858889 | 6/2000 |
| DE | 20007908 | 1/2001 |

OTHER PUBLICATIONS

Oberg, E.; Jones, F.D.; Horton, H.L.; Ryffell, H.H., Machinery's Handbook, 2000, Industrial Press, 26th Edition, pp. 1578.*
Collins A. Jack, Mechanical Design of Machine Elements and Machines, 2003, John Wiley & Sons, Inc., pp. 468.*

* cited by examiner

*Primary Examiner*—Thomas C Barrett
*Assistant Examiner*—Nicholas Woodall
(74) *Attorney, Agent, or Firm*—Howard & Howard Attorneys PLLC

(57) ABSTRACT

A self drilling bone screw (10) comprises a shank (16) provided with a thread (14), a pitch of the thread (14) being in the region of approximately 0.7 to 1.0 mm. A tip angle is selected such that a thread flank (20) of a first flight (22) adjacent to a tip (18) of the bone screw (10) is arranged at a distance of approximately 0.2 to 0.5 mm from the tip (18) of the bone screw (10).

13 Claims, 2 Drawing Sheets

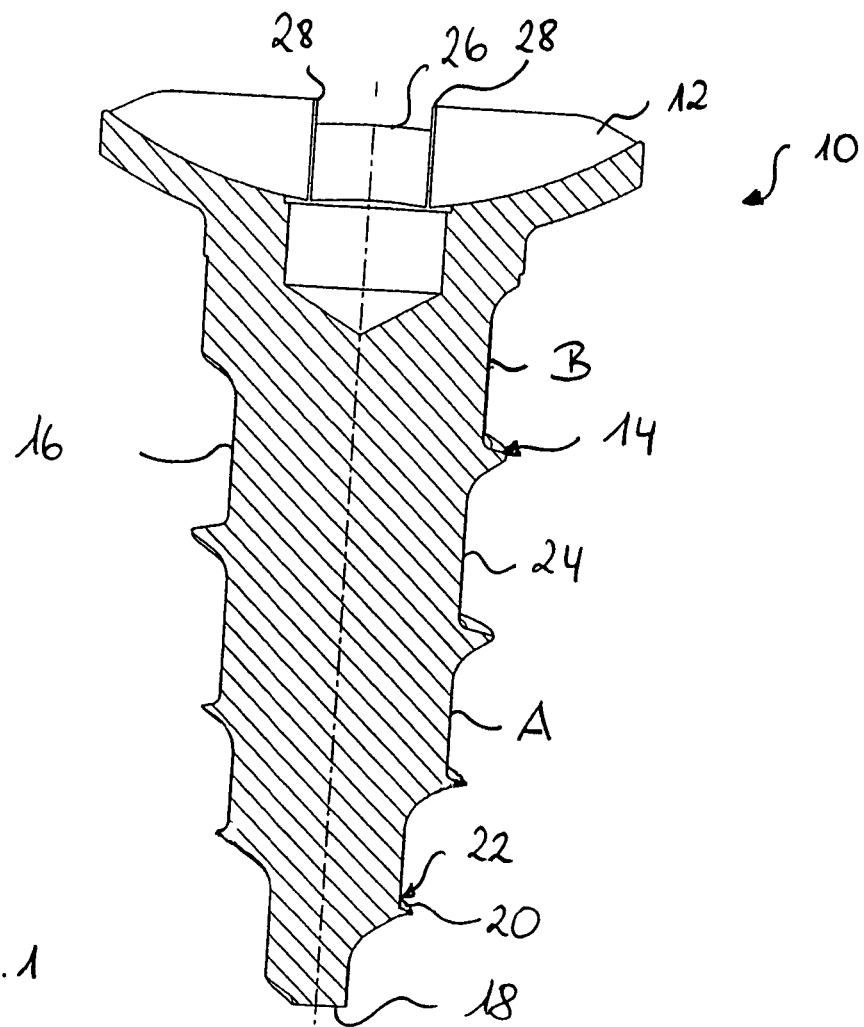
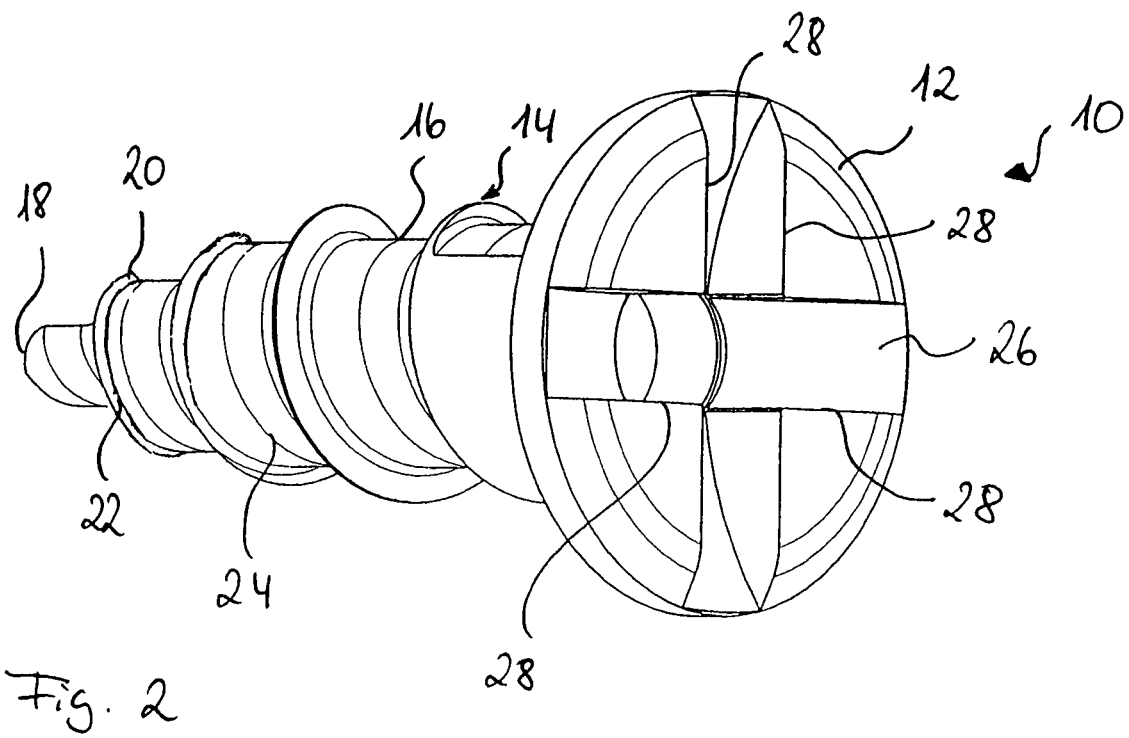
Fig. 1
Fig. 2

SELF-DRILLING BONE SCREW

CROSS-REFERENCE TO RELATED APPLICATIONS

This application claims priority under 35 U.S.C. §119(a) to German Patent Application No. 103 61 044.8, filed on Dec. 23, 2003.

FIELD OF THE INVENTION

The invention relates to a self-drilling bone screw which comprises a shank provided with a thread, in particular for use in surgical operations in the craniofacial region.

BACKGROUND TO THE INVENTION

It is frequently necessary in surgical operations in the craniofacial region to reposition and then to fix, after the end of the surgical operation, a fragment of the skull sawn-out from the skull bone or alternatively, to substitute areas of the bone removed during the operation with a plate consisting of a suitable biocompatible material, such as for example titanium. As in the craniofacial region no large forces act on the corresponding fixing points, the rigidity and in particular the pull-out resistance of the fixing plays only a subordinate role in this anatomical region. To fasten the sawn-out fragment of the skull or the plate in the desired position, self-drilling bone screws are therefore preferably used. Such self-drilling bone screws have the advantage that they can be screwed relatively easily into a bone or a bone fragment by the surgeon, without preliminary treatment of the bone or the bone fragment being required, for example by the insertion of a bore or the like.

To be easily screwed into the bone or the bone fragment, self-drilling bone screws generally have a screw tip with a smallest possible tip angle. In particular with longer screws the problem frequently occurs, however, that the screw tip bends or even breaks when screwed into the bone or the bone fragment.

A self-drilling bone screw is known from U.S. Pat. No. 5,925,048 which comprises a head and a shank provided with a thread. The screw has a total length of 4 to 14 mm and a tip angle of 45 to 50°.

The object of the invention is to provide a self-drilling bone screw which can be easily and rapidly screwed into a bone or a bone fragment and in which, at the same time, bending or even breaking of the screw tip can be reliably avoided when screwing in.

SUMMARY OF THE INVENTION

This object is achieved according to the invention by proposing a self-drilling bone screw with a shank provided with a thread, where the thread has a pitch of approximately 0.7 to 1.0 mm and where a tip angle is selected such that a thread flank of a first flight adjacent to a tip of the bone screw is arranged at a distance of approximately 0.2 to 0.5 mm from the tip of the bone screw. The thread can be constructed as a left-hand thread or a right-hand thread.

With a pitch of approximately 0.7 to 1.0 mm the tip angle is preferably within a region of approximately 34 to 43°. Depending on the pitch selected, a tip angle within a region of approximately 35 to 38° can also be advantageous.

In one embodiment of the bone screw according to the invention the thread has a pitch of approximately 0.8 to 0.9 mm. A relatively large pitch within this region allows the screw to be rapidly screwed into a bone or a bone fragment. Screws in which the pitch is approximately 0.8 mm or approximately 0.9 mm and the tip angle approximately 43° or approximately 36° have particularly good cutting behaviour.

The self-drilling bone screw according to the invention typically has a length of approximately 3 to 7 mm. In one embodiment of the invention the length of the screw is approximately 3.5 to 5 mm. A bone screw of this length is very well suited for use in the craniofacial region.

A diameter of a thread core of the bone screw according to the invention can be in a region of approximately 1.0 to 1.3 mm. A core or crest diameter of approximately 1.05 to 1.2 mm is advantageous. Such a relatively large crest diameter selected ensures that the screw does not break when screwed into the bones or the bone fragment. With a screw length of 4.5 mm a core or crest diameter of 1.1 mm has proved to be advantageous.

In a further embodiment of the self-drilling bone screw according to the invention, the thread core is of conical construction. As a result, the required torque to screw in the first flights is reduced, so that the screw can be particularly easily screwed into the bone or the bone fragment. The thread core can also be of cylindrical construction.

The bone screw may comprise a head. In the region of the head a torque receiving structure such as a slot or a cross recess can be arranged. Hexagonal or Torx structures can also be used. The torque receiving structure preferably comprises square-shaped edges. The bone screw can then be screwed in by using a conventional screwdriver used during surgical operations. The square-shaped edges prevent the screwdriver from slipping out of the torque receiving structure, in particular when the screwdriver has to be offset or tilted.

In one embodiment of the bone screw according to the invention, the head of the bone screw has a diameter of approximately 2.0 to 3.0 mm. A screwhead diameter of approximately 2.55 to 2.65 mm is advantageous. This relatively large screwhead diameter allows the surgeon to transfer a large torque onto the screw via the screwdriver blade. As a result it is easier to screw the screw into the bone or the bone fragment.

The screwhead may however also be omitted. In such a case, the screw would only consist of a thread and a shank. The shank can have a torque receiving structure.

The bone screw may be positioned to penetrate a bore constructed in a plate. The plate can for example be a plate for connecting two or more bones or bone fragments which can be screwed to the bone fragments by means of the bone screw according to the invention. Alternatively, the plate can also be provided to replace a bone fragment removed during an operation and be fixed to bone regions adjacent to the removed bone fragment by means of the bone screw according to the invention. A lower face of the head of the bone screw can be adapted to a recess formed in a surface of the plate. By countersinking the head of the bone screw according to the invention into the recess formed in the surface of the plate, the plate/screwhead elements have a relatively low height. The provision of these elements with a relatively low height of 0.6 to 0.7 mm has the advantage that a plate implanted in a part of the body with only a small amount of soft tissue, is not felt under the skin by a patient whose skull has been operated on.

In one embodiment of the self-drilling bone screw according to the invention which is particularly simple and inexpensive to manufacture, the lower face of the head of the bone screw is of conical construction. The screwhead can then be countersunk into a conically formed recess in the surface of the plate which is also simple and inexpensive to manufacture.

BRIEF DESCRIPTION OF THE DRAWINGS

Further advantages and embodiments of the invention will be revealed in the following description of preferred embodiments and in the drawings, in which:

FIG. 1 is a cross-sectional view of a self-drilling bone screw according to the invention;

FIG. 2 is a perspective view of the self-drilling bone screw according to the invention;

DESCRIPTION OF PREFERRED EMBODIMENTS

Figure 3:
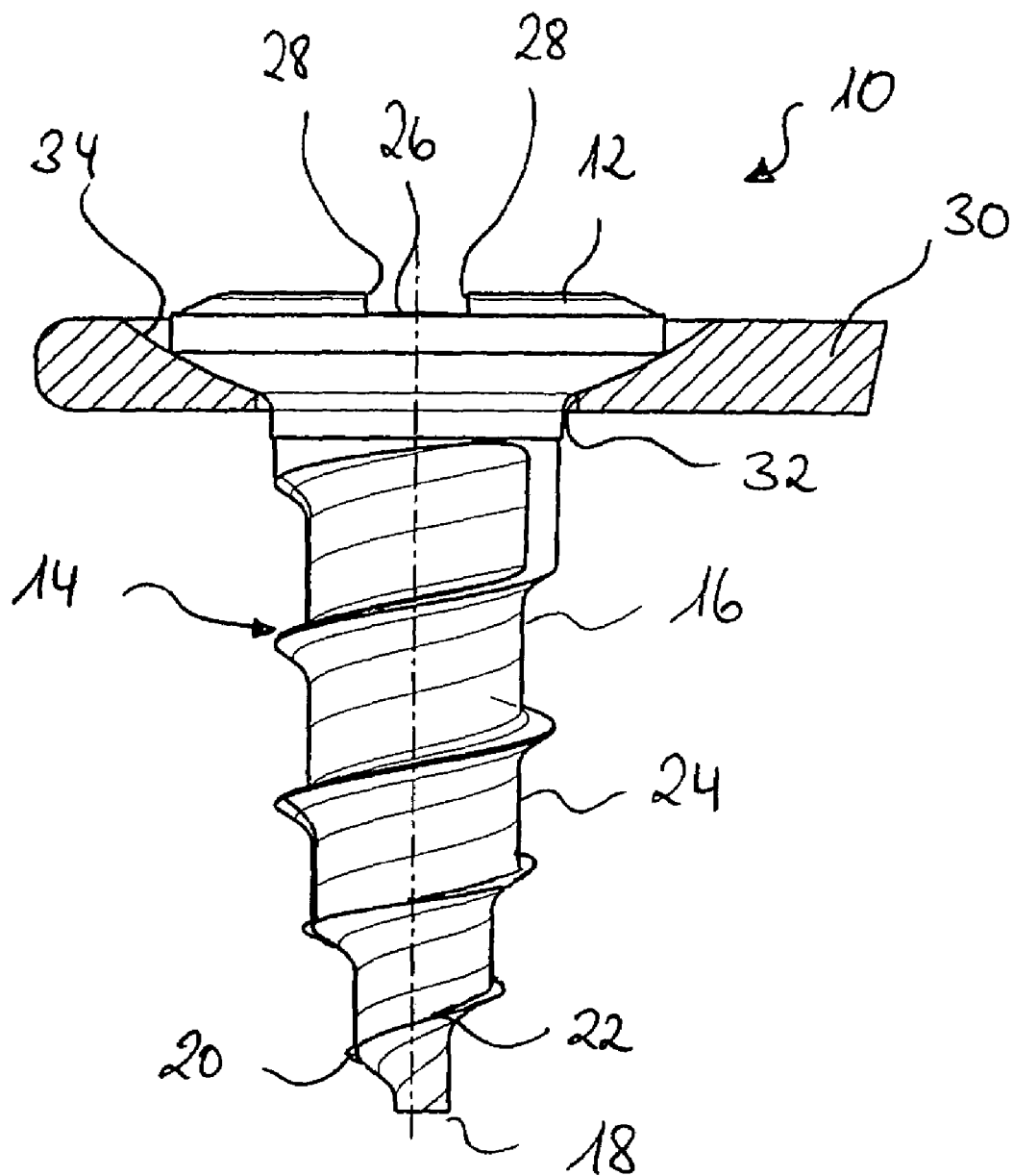
FIG. 3 is a partial cross-sectional view in which the self-drilling bone screw according to the invention penetrates a bore constructed in a plate.

A self-drilling bone screw 10 shown in FIGS. 1 to 3 comprises a head 12 and a shank 16 provided with a thread 14. In the embodiment shown the screw 10 provided for use in surgical operations in the craniofacial region has a total length of approximately 5 mm. It is however understood that, depending on the desired application, other screw lengths, for example 4 mm can also be selected. To allow the screw 10 to be rapidly screwed into a bone or a bone fragment, the thread 14 has a pitch of approximately 0.9 mm.

A tip angle of a screw tip 18 is selected such that the start of a thread flank 20 of a first flight 22 adjacent to the screw tip 18 is arranged at a distance of approximately 0.32 mm from the screw tip 18, the front tip region being constructed without a flank. To ensure this, the tip angle is approximately 36° in the embodiment of the bone screw 10 shown. By adapting the tip angle to the pitch it is ensured that the screw tip 18 is dimensioned such that bending or even breaking the screw tip 18 is reliably avoided when the screw 10 is screwed into a bone or a bone fragment. At the same time, the first thread flank 20 arranged at a distance of approximately 0.32 mm from the screw tip 18 ensures that the screw 10 is 'pulled' into the bone when screwed in, whereby good cutting behaviour of the screw 10 is ensured.

In a further embodiment not shown in the Figures, the pitch is approximately 0.8 mm, the thread flank of the first thread attached to the screw tip being also arranged at a distance of approximately 0.32 mm from the screw tip. The tip angle of this screw is approximately 43°.

To reduce the torque required to screw the first flights of the thread 14 into the bone or the bone fragment, a thread core 24 of the screw 10 is of conical construction. In the position shown in FIG. 1 by A, the thread core has a diameter of approximately 1.1 mm. At the position shown in FIG. 1 by B the core diameter is approximately 1.15 mm. This relatively large crest diameter ensures that the screw does not break when screwed into the bone or the bone fragment.

A cross recess 26 is provided on the head 12 of the bone screw 10 to receive a blade of a conventional screwdriver generally used during surgical operations. In order to prevent the blade from slipping out of the cross recess 26, particularly when the screwdriver has to be offset, the cross recess is constructed with square-shaped edges 28.

The head 12 of the bone screw 10 has a diameter of approximately 2.6 mm. This relatively large screwhead diameter allows the surgeon to transfer a large torque onto the screw 10 via the screwdriver blade. As a result the screw 10 is more easily screwed into the bone or the bone fragment.

As is shown in FIG. 3, in the implanted state the bone screw 10 is provided to penetrate a bore 32 constructed in a plate 30. The plate 30 can for example be a retaining plate to connect two or more bone fragments which are screwed onto the bone fragments by means of the bone screw 10. Alternatively, the plate 30 can also be provided to replace a bone fragment removed during an operation and to be fixed to bone regions adjacent to the removed bone fragment by means of the bone screw 10.

A lower face of the head 12 of the bone screw 10 is, as is best seen in FIGS. 1 and 3, of conical construction. As a result the screwhead 12 can be countersunk into a recess 34 constructed in a surface of the plate 30 and which is also conical-shaped. By countersinking the screwhead 12 into the recess formed in the surface of the plate, the plate/screwhead elements have a relatively low height of approximately 0.65 mm. As a result, it is ensured that the plate implanted in a part of the body with only a small amount of soft tissue, is not felt under the skin by a patient whose skull has been operated on.

The application of the aforementioned bone screw 10 is not restricted to the craniofacial field. The bone screw 10 may for example also be used in the hand region.

The invention claimed is:

1. A self-drilling bone screw comprising:
   a head; and
   a shank extending from the head and having a thread with a pitch of approximately 0.7 to 1.0 mm, the shank having a tip with a tip angle selected such that a thread flank of a first flight of the thread adjacent to the tip is arranged at a distance of approximately 0.2 to 0.5 mm from the tip.

2. The self-drilling bone screw according to claim 1, wherein the thread has a pitch of approximately 0.8 to 0.9 mm.

3. The self-drilling bone screw according to claim 1, wherein the bone screw has a length of approximately 3 to 7 mm.

4. The self drilling bone screw according to claim 1, wherein the tip angle is within a range of approximately 34 to 43°.

5. The self-drilling bone screw according to claim 1, wherein the thread has a core with a diameter of approximately 1.0 to 1.3 mm.

6. The self-drilling bone screw according to claim 1, wherein the thread has a core with a diameter of approximately 1.05 to 1.2 mm.

7. The self-drilling bone screw according to claim 1, wherein the thread has a core with a conical shape.

8. The self-drilling bone screw according to claim 1, wherein the head includes a torque receiving structure, the torque receiving structure comprising square-shaped edges.

9. The self-drilling bone screw according to claim 8, wherein the head has a diameter of approximately 2.0 to 3.0 mm.

10. A self-drilling bone screw comprising:
    a head;
    a shank extending from the head to a distal end, the shank having a thread with a pitch of approximately 0.7 to 1.0 mm; and
    a tip disposed at the distal end of the shank with a tip angle of approximately 34 to 43° and a thread flank of a first flight of the thread adjacent to the tip arranged at a distance of approximately 0.2 to 0.5 mm from the tip.

11. An implant system comprising:
    a self-drilling bone screw having a head and a shank extending from the head, the shank having a thread with a pitch of approximately 0.7 to 1.0 mm and a tip with a tip angle selected such that a thread flank of a first flight of the thread adjacent to the tip is arranged at a distance of approximately 0.2 to 0.5 mm from the tip; and a bone plate defining a bore and a recess disposed about the bore, the head of the bone screw adapted to rest in the recess and the shank of the bone screw adapted to penetrate the bore.

12. The implant system according to claim 11, wherein the head of the bone screw has a lower face with a conical shape.

13. A method of inserting a bone screw in a craniofacial bone or in a hand bone, comprising:

providing a self-drilling bone screw comprising a shank having a thread with a pitch of approximately 0.7 to 1.0 mm, the shank having a tip with a tip angle selected such that a thread flank of a first flight of the thread adjacent to the tip is arranged at a distance of approximately 0.2 to 0.5 mm from the tip;

providing a bone plate having a bore; and attaching the bone plate to the bone by screwing the bone screw into the bone such that the bone screw penetrates the bore in the bone plate.

* * * * *